United States Patent
Humes (10) Patent No.: US 6,653,131 B2
(45) Date of Patent: Nov. 25, 2003

(54) METHOD OF TREATING SYSTEMIC INFLAMMATORY RESPONSE SYNDROME

(75) Inventor: H. David Humes, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 244 days.

(21) Appl. No.: 09/941,987

(22) Filed: Aug. 30, 2001

(65) Prior Publication Data

US 2003/0118559 A1 Jun. 26, 2003

(51) Int. Cl.[7] .................................................. C12N 5/00
(52) U.S. Cl. ...................... 435/369; 424/93.7; 435/325; 435/395; 435/400; 604/4.01; 604/5.02; 604/6.04; 623/23.65
(58) Field of Search ................................. 435/400, 325, 435/395, 369; 623/23.65; 424/93.7; 604/4.01, 5.02, 6.04

(56) References Cited

U.S. PATENT DOCUMENTS

| | | | |
|---|---|---|---|
| 3,734,851 A | 5/1973 | Matsumura | |
| 4,242,460 A | 12/1980 | Chick et al. | |
| 4,354,933 A | 10/1982 | Lester | |
| 5,360,790 A | 11/1994 | Humes | |
| 5,429,938 A | 7/1995 | Humes | |
| 5,516,680 A | 5/1996 | Naughton et al. | |
| 5,549,674 A | 8/1996 | Humes et al. | |
| 5,686,289 A | 11/1997 | Humes et al. | |
| 6,060,270 A | 5/2000 | Humes | |
| 6,150,164 A | 11/2000 | Humes | |

FOREIGN PATENT DOCUMENTS

| | | |
|---|---|---|
| GB | 1 479 002 | 6/1974 |
| WO | WO 89/01967 | 3/1989 |
| WO | WO 91/00119 | 1/1991 |
| WO | WO 92/07615 | 5/1992 |
| WO | WO 93/17696 | 9/1993 |

OTHER PUBLICATIONS

H. David Humes et al., *Replacement of Renal Function in Uremic Animals with a Tissue–Engineered Kidney*, Nature Biotechnology, vol. 17, pp. 451–455, May 1999.
Roger C. Bone, *Systemic Inflammatory Responses Syndrome: A Unifying Concept of Systemic Inflammation, Sepsis and Multiorgan Failure*, 1997, pp. 3–10.
H. David Humes et al., *Tissue Engineering of a Bioartificial Renal Tubule Assist Device: In Vitro Transport and Metabolic Characteristics*, Kidney International, vol. 55 (1999), pp. 2502–2514.
H. David Humes, *Bioartificial Kidney for Full Renal Replacement Therapy*, Seminars in Nephrology, vol. 20, No. 1, Jan. 2000, pp. 71–82.
John M. Walker et al, *The Language of Biotechnology*, 1988, p. 126.
R. Ian Freshney, *Culture of Animal Cells, A Manual of Basic Technique*, Second Edition, 1987, pp. 1–13, and pp. 197–206.
Sherrill M. MacKay et al., *Tissue Engineering of a Bioartificial Renal Tubule*, ASAIO Journal, vol. 44, No. 3, May–Jun. 1998, pp. 179–183.
Sally Pobojewski, *U Researchers Unveil Component of Bio–Artificial Kidney*, The University Record, May 24, 1999.
Charles Natansonet et al., *Role of Endotodemia in Cardiovascular Dysfunction and Mortality*, The Journal of Clinical Investigation, Inc., vol. 83, Jan. 1989, pp. 243–251.
Bradley D. Freeman et al., *Continuous Ateriovenous Hemofiltration Does Not Improve Survival in a Canine Model of Septic Shock*, Journal of the American College of Surgeons, Mar. 1995, vol. 180, pp. 286–291.
J. A. Kellum, *Immunomodulation in Sepsis: The Role of Hemofiltration*, Minerva Anestesiologica, vol. 65, No. 6, pp. 410–418.
Gordon R. Bernard, M.D. et al., *Efficacy and Safety of Recombinant Human Activated Protein C for Severe Sepsis*, The New England Journal of Medicine, vol. 344, No. 10, Mar. 8, 2001, pp. 699–709.
Diep D. Tranet et al., *Age, Chronic Disease, Sepsis, Organ System Failure, and Mortality in a Medical Intensive Care Unit*, Critical Care Medicine, vol. 18, No. 5, pp. 474–479, May 1990.
S. C. Donnellyet et al., *Mediators, Mechanisms and Mortality in Major Trauma*, Resuscitation, vol. 28, pp. 87–92, 1994.
Roger C. Bone, M.D. et al., *A Controlled Clinical Trial of High–Dose Methylprednisolone in the Treatment of Severe Sepsis and Septic Shock*, The New England Journal of Medicine, vol. 317, No. 11, pp. 653–658.
K. D. Horn, *Evolving Strategies in the Treatment of Sepsis and Systemic Inflammatory Response Syndrome (SIRS)*, Q. J. Med, 1998, vol. 91, pp. 265–277.
Michael R. Pinsky, *Serum Cytokine Levels in Human Septic Shock*, Chest, vol. 103, No. 2, Feb. 1993, pp. 565–575.
Claire Marty et al., *Circulating Interleukin–8 Concentrations in Patients with Multiple Organ Failure of Septic and Nonseptic Origin*, Critical Care Medicine, vol. 22, No. 4, pp. 673–679, Apr. 1994.
Pierre Damas, M.D., Ph.D. et al., *Tumor Necrosis Factor and Interleukin–1 Serum Levels During Severe Sepsis in Humans*, Critical Care Medicine, vol. 17, No. 10, pp. 975–978, Oct. 1989.
Charles A. Dinarello, *The Proinflammatory.Cyotkines Interleukin–1 and Tumor Necrosis Factor and Treatment of the Septic Shock Syndrome*, The Journal of Infectious Diseases, 1991: 163, pp. 1177–1184.

(List continued on next page.)

Primary Examiner—Leon B. Lankford, Jr.
(74) Attorney, Agent, or Firm—Oblon, Spivak, McClelland, Maier & Neustadt, P.C.

(57) ABSTRACT

A method for treating systemic inflammatory response syndrome (SIRS) by contacting the bodily fluid of a patient with renal tubule cells outside of the kidney.

23 Claims, 9 Drawing Sheets

OTHER PUBLICATIONS

Thierry Calandra et al., *Prognostic Values of Tumor Necrosis Factor/Cachectin, Interleukin–1, Interferon–α, and Interferon–y in the Serum of Patients with Septic Shock*, The Journal of Infectious Diseases, 1990: 161, pp. 982–987.

J. X. Jiang et al., *Plasma Cytokines and Endotoxin Levels in Patients with Severe Injury and Their Relationship With Organ Damage, Injury*, vol. 28, No. 8, pp. 509–513, 1997.

Dorothy Breen et al., *Acute Renal Failure as a Part of Multiple Organ Failure: The Slippery Slope of Critical Illness*, Kidney International, vol. 53, Suppl. 66 (1998), pp. S–25–S33.

Mark J. Sarnak et al., *Mortality Caused by Sepsis in Patients with End–Stage Renal Disease Compared with the General Population*, Kidney International, vol. 58 (2000), pp. 1758–1764.

Matthias Girndt et al., *Production in Interleukin–6, Tumor Necrosis Factor α and Interleukin–10 in vitro Correlates with the Clinical Immune Defect in Chronic Hemodialysis Patients*, Kidney International, vol. 47 (1995), pp. 559–565.

Matthias Girndt et al., *Impaired Cellular Immune Function in Patients with End–Stage Renal Failure*, Nephrol Dial Transplant, (1999) 14: 2807–2810.

Melissa K. Thomas, M.D., Ph.D. et al., *Hyptovitaminosis D in Medical Inpatients*, The New England Journal of Medicine, vol. 338, No. 12, Mar. 19, 1998, pp. 777–783.

Roger C. Bone, M.D., *Why Sepsis Trials Fail*, JAMA, Aug. 21, 1996, vol. 276, No. 7, pp. 565–566.

Roger C. Bone, M.D., *Toward a Theory Regarding the Pathogenesis of the Systemic Inflammatory Response Syndrome: What we Do and Do Not Know about Cytokine Regulation*, Crit Care Med, 1996, vol. 24, No. 1, pp. 163–172.

C. Erik Hack et al., *Interleukin–8 in Sepsis: Relation to Shock and Inflammatory Mediators*, Infection and Immunity, Jul. 1992, vol. 60, No. 7, p. 2835–2842.

Roger C. Bone, M.D., *Immunologic Dissonance: A Continuing Evolution in Our Understanding of the Systemic Inflammatory Response Syndrome (SIRS) And the Multiple Organ Dysfunction Syndrome (MODS)*, Ann Intern Med., 1996, vol. 125, p. 680–687.

Roger C. Bone, M.D., *Sepsis: A New Hypothesis for Pathogenesis of the Disease Process*, Chest, vol. 112, No. 1, Jul. 1997, pp. 235–243.

John H. Reeveset et al., *Continuous Plasmafiltration in Sepsis Syndrome*, Crit Care Med, 1999, vol. 27, No. 10, pp. 2096–2104.

An S. De Vriese et al., *Continuous Renal Replacement Therapies in Sepsis: Where are the Data?*, Nephrol Dial Transplant, (1998), vol. 13, pp. 1362–1364.

Jean–Louis Vincent, M.D. et al., *Phase II Multicenter Clinical Study of the Platelet–Activating Factor Receptor Antagonist BB–882 in the Treatment of Sepsis*, Crit Care Med, vol. 28, No. 3 2000, pp. 638–642.

Zenaide M. N. Quezadoet et al., *New Strategies for Combatting Sepsis: The Magic Bullets Missed the Mark . . . But the Search Continues*, Tibtech, Feb. 1995, vol. 13, pp. 56–63.

John W. Christman, M.D., *Strategies for Blocking the Systemic Effects of Cytokines in the Sepsis Syndrome*, Critical Care Medicine, vol. 23, No. 5, pp. 955–963, 1995.

M. L. Kielaret et al., *The Liver Regulates Renal Ischemic Injury: A Possible Role for Renal IL6 and Hepatic IL 10?*, Abstract.

Kevin P. Lallyet et al., *The Role of Anti–Tumor Necrosis Factorα and Interleukin–10 in Protecting Murine Neonates from Escherichia coli, Sepsis*, Journal of Pediatric Surgery, vol. 35, No. 6, Jun. 2000, pp. 852–855.

Keith R. Walley et al., *Balance of Inflammatory Cytokines Related to Severity and Mortality of Murine Sepsis*, Infection and Immunity, No. 1996, pp. 4733–4738, vol. 64, No. 11.

Tetsuya Matsumoto et al., *Effect of Interleukin–10 on Gut–Derived Sepsis Caused by Pseudomonas Aeruginosa in Mice*, Antimicrobial Agents and Chemotherapy, Nov. 1998, vol. 42, No. 11, p. 2853–2857.

Arnaud Merchant et al., *Interleukin–10 Controsl Interferon–y and Tumor Necrosis Factor Production During Experimental Endotoxemia*, Eur. J. Immunol., 1994, vol. 24, pp. 1167–1171.

Sherril M. MacKay et al., *Tissue Engineering of a Bioartificial Renal Tubule*, ASAIO Journal, 1998, pp. 179–183.

Ziad A. Massy, *Reversal of Hyperhomocyst(e) Inaemia in Chronic Renal Failure—Is Folic or Folinic Acid the Answer?*, Nephrol Dial Transplant, (1999), vol. 14, pp. 2810–2812.

Raymound Vanholder et al., *p–Cresol: A Toxin Revealing Many Neglected But Relevant Aspects of Uraemic Toxicity*, Nephol Dial Transplant (1999) vol. 14, pp. 2813–2815.

Jürgen Bommer, *Saving Erythropoietin by Administering L–Carnitine?*, Nephrol Dial Transplant, (1999), vol. 14, pp. 2819–2821.

Max Dratwa, *Pre–Emptive (CAPD—What Are the Arguments?*, Nephrol Dial Transplant, (1999), vol. 14, pp. 2822–2823.

Bart D. Maes et al., *Anti–Interleukin–2 Receptor Monoclonal Antibodies in Renal Transplantaion*, Nephrol Dial Transplant, (1999) vol. 14, pp. 2824–2826.

Andras Mogyorosi et al., *GLUT1 and TGF–β: The Link Between Hyperglycaemia and Diabetic Nephropathy*, Nephrol Dial Transplant, (1999), vol. 14, pp. 2827–2829.

R. Montesano et al., *Induction of Epithelial Tubular Morphogenesis in Vitro by Fibroblast–Derived Soluble Factors*, Cell, vol. 66, Aug. 23, 1991, pp. 697–711.

H. David Humes et al., *Effects of Transforming Growth Factor–β, Transforming Growth Factor–α, and Other Growth Factors on Renal Proximal Tubule Cells*, Laboratory Investigation, vol. 64, No. 4, pp. 538–545, 1991.

Fiona M. Wattet et al., *Out of Eden: Stem Cells and Their Niches*, Science, vol. 287, Feb. 25, 2000, pp. 1427–1430.

Qais Al–Awqati, *Cellular and Molecular Mechanisms of Renal Development and Tubulogenesis*, Current Science,, 1062, 4813, Oct., pp. 53–58.

Stuart H. Orkin, M.D., *Report and Recommendations of the Panel to Assess the NIH Investment in Research on Gene Therapy*.

Tze Kin Ip et al., *Renal Epithelial–Cell–Controlled Solute Transport Across Permeable Membranes as the Foundation for a Bioartificial Kidney*, Artificial Organs, vol. 13, No. 1, pp. 58–65, 1989.

METHOD OF TREATING SYSTEMIC INFLAMMATORY RESPONSE SYNDROME

BACKGROUND OF THE INVENTION

1. Field of the Invention

The present invention relates to a method for treating systemic inflammatory response syndrome (SIRS) by contacting the bodily fluid of a patient with renal tubule cells outside of the kidney.

2. Background of the Invention

The mortality from sepsis complicated by renal failure remains extremely high despite the application of modem renal replacement therapy. The systemic inflammatory response syndrome, or SIRS, is a catastrophic sequela of a variety of clinical insults, including infection, pancreatitis, and cardiopulmonary bypass, and claims over a quarter million lives in the US each year. [Refs. 1, 2, 3, 4, 5, 6].

The exceptionally high mortality associated with the syndrome is due in part to the development of the highly lethal multiple system organ failure syndrome, or MSOF, in a subset of patients with SIRS. The sequential failure of organ systems apparently unrelated to the site of the initial insult has been correlated with altered plasma cytokine levels observed in sepsis. [Refs. 7, 8, 9, 10, 11, 12].

The mortality is especially high in patients with MSOF and acute renal failure (ARF). The excess mortality seen in patients with sepsis and ARF is not ameliorated by conventional renal replacement therapy, which treats volume overload, uremia, acidosis, and electrolyte derangements. [Refs. 13, 4].

Accordingly, there remains an ongoing need for new methods for treating patients with SIRS.

SUMMARY OF THE INVENTION

It is an object of the present invention to provide methods for treating patients with SIRS.

The present invention is based, in part, on the discovery that a body fluid of a patient with SIRS can be contacted with renal tubule cells outside of the kidney. As a result of this contact, the tubule cells introduce mediators into the body fluid. After contact with the tubule cells, at least a portion of the body fluid is recirculated to the patient, where the mediators induce a response in the patient which leads to amelioration of the SIRS state. As a result of this contact, the tubule cells introduce mediators into and/or reabsorb mediators from the body fluid.

Accordingly, the present invention provides a method of treating a patient with SIRS, comprising:

contacting, outside of the kidney, at least a portion of a body fluid of the patient with renal tubule cells.

The present invention also provides a method of treating a patient with SIRS, comprising:

removing a portion of body fluid from the patient, contacting the removed body fluid with renal tubule cells, and returning at least a portion of the body fluid which has been contacted with the renal tubule cells to the patient.

BRIEF DESCRIPTION OF THE FIGURES

A more complete appreciation of the invention and many of the attendant advantages thereof will be readily obtained as the same becomes better understood by reference to the following Figures in conjunction with the detailed description below.

DETAILED DESCRIPTION OF THE INVENTION

The present invention is based, in part, on the inventors' discovery that contacting a body fluid of a patient with SIRS and then returning at least a portion of the treated body fluid to the patient results in amelioration of SIRS. Without being limited to any particular theory, it appears that the cells may provide immunomodulatory effects by influencing systemic cytokine patterns. At the same time, the hemodynamic status of the patient improves as well.

As mentioned above, the patient to be treated according to the present invention has SIRS. In one embodiment, the patient is afflicted with sepsis. In this embodiment, the patient may have been diagnosed with sepsis by a healthcare provider according to diagnostic procedures well-known to those skilled in the art. In another embodiment, the patient has MSOF. Criteria for diagnosing these conditions is described in, for example, Roger C. Bone, in *Sepsis and Multiorgan Failure,* Alan M. Fein et al., Eds., Williams & Wilkins, Baltimore, Md., 1997, pp. 3–10, incorporated herein by reference.

The patient may be a human or a non-human animal, such as a mammal. Exemplary non-human animals include dogs, cats, horses, cows, sheep, goats, and pigs.

An important feature of the present invention is that the body fluid of the patient is contacted with renal tubule cells. It is important to note that the body fluid of the patient is contacted with renal tubule cells outside of the kidney. In the present invention, the natural flow of the body fluid is interrupted so that the fluid can interact with the renal tubule cells. After this contact, the body fluid is returned to the course of natural flow in the patient's body. Thus, the present invention is distinct from the natural physiological processes which occur in the kidney.

Figure 1:
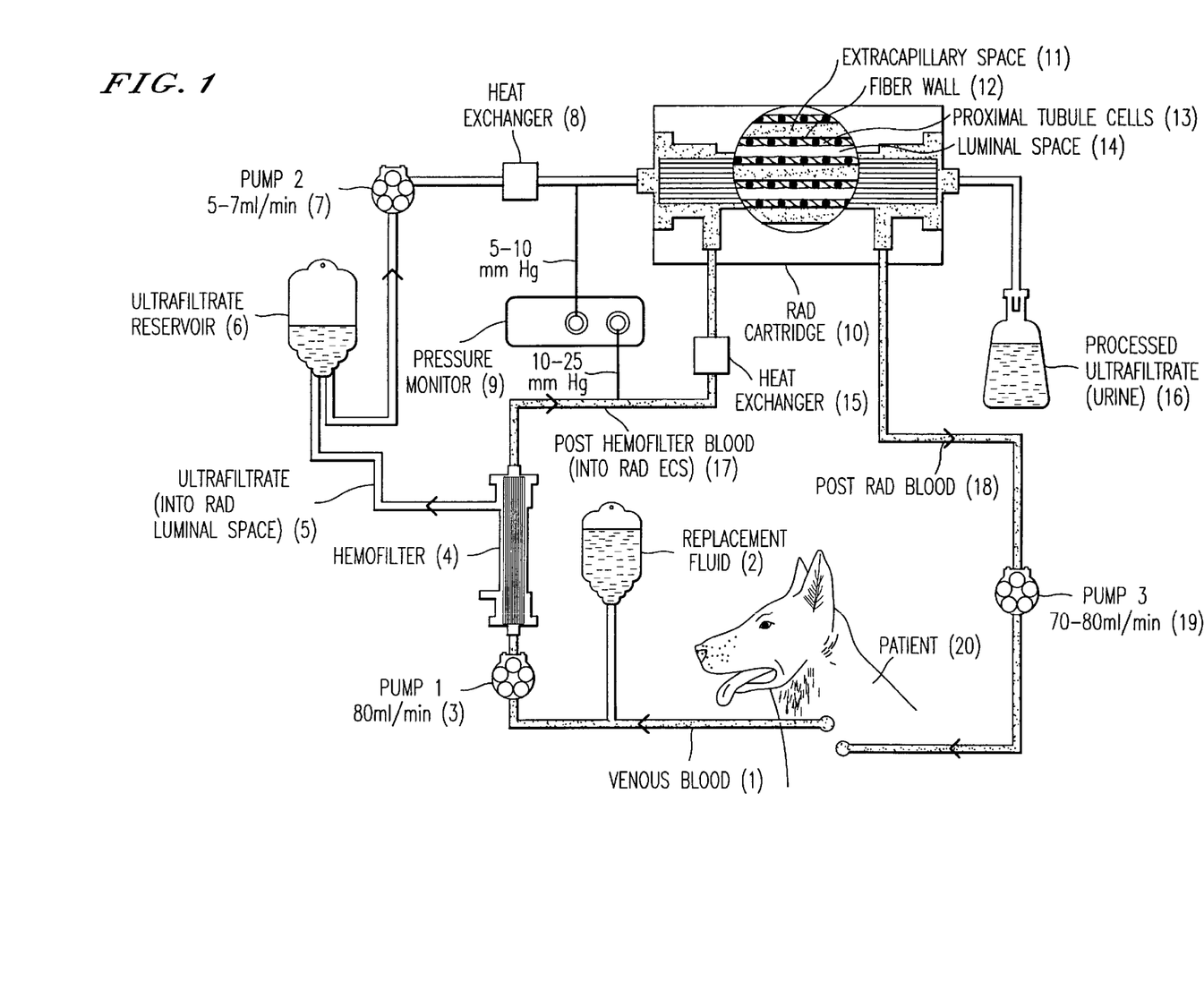
FIG. 1: RAD perfuision chart.

Methods and devices for contacting a body fluid with renal tubule cells and then returning the treated fluid to the patient are well-known in the art. See, for example, references 18, 19, 20, 36, and U.S. Pat. No. 6,150,164, all of which are incorporated herein by reference in their entirety. In a particularly preferred embodiment of the invention, the body fluid of the patient is contacted in with the renal tubule cells in a renal tubule assist device (RAD). As used herein, the term "renal tubule assist device" refers to a device which contains (1) renal tubule cells and (2) an inlet and outlet for the body fluid, where the body fluid is contacted with the renal tubule cells inside the device. Such a device is described in detail in the publications cited immediately above. An example of a suitable RAD is shown in FIG. 1 as element (10) in the a circuit shown therein.

In addition to the methods described in the publications cited immediately above, the renal tubule cells may also be grown on solid or porous microcarrier beads. Examples of suitable microcarrier beads include micropourous gelatin and collagen-coated dextran. In this embodiment, the cells can be grown on the beads. Then, the cells can be detached from the beads and be seeded in the RAD. In another embodiment, the cells on the beads can be used in the extracapillary space of a sepsis treating cartridge on microcarrier beads as opposed to single monolayers along the inner surface of hollow fibers. Thus, a body fluid of a patient could be perfused into a cartridge containing these cells in this formulation for exposure to the patient's fluid and respond with mediators that would alter the SIRS condition.

The tubule cells may be obtained from a human or a non-human animal source. The non-human animal is preferably a mammal. Suitable examples of non-human cells are porcine, rat, dog, mouse, or rabbit tubule cells. Transformed tubule cells may also be used in the present invention. Such cells are described in, for example, U.S. Pat. No. 6,150,164.

The body fluid may be blood, plasma, or ultrafiltrate of plasma. Venous blood is particularly preferred. Arterial blood may also be used.

In one embodiment of the invention, the body fluid of the patient is contacted in with the renal tubule cells ex vivo, i.e, outside of the body of the patient. In an alternative embodiment, the body fluid is contacted in with the renal tubule cells inside the body of the patient.

In one embodiment, the renal tubule assist device is ex vivo. Alternatively, the renal tubule assist device is implanted in the patient.

The patient may also be afflicted with renal disease, for example acute renal failure or chronic renal failure. Such a patient may be afflicted with end-stage renal disease. Such a patient may also be on hemo- or peritoneal dialysis.

An example of a specific embodiment of the present invention is shown in FIG. 1. In this embodiment, venous blood (1) from the patient (20) afflicted with sepsis is removed. The removed blood (1) is sent via pump (3) to hemofilter (4). Replacement fluid (2) is added to the 10 venous blood (1) during transport to hemofilter (4). From hemofilter (4), the ultrafiltrate (5) is passed to ultrafiltrate reservoir (6) and the post hemofilter blood (17) is sent to the RAD cartridge (10) after passing through heat exchanger (15). The ultrafiltrate is transferred to the RAD cartridge (10) via pump (7) and heat exchanger (8). Pressure monitor (9) is used to monitor the pressure in the input flows to cartridge (10). Cartridge (10) comprises extracapillary 15; space (11), fiber wall (12), proximal tubule cells (13), and luminal space (14). Post RAD blood (18) is then transferred via pump (19) back to patient (20). The processed ultrafiltrate (16) is collected from the RAD cartridge (10).

EXAMPLES

Having generally described this invention, a further understanding can be obtained by reference to certain specific examples which are provided herein for purposes of illustration only and are not intended to be limiting unless otherwise specified.

Example 1

Bioartificial Kidney Alters Cytokine Response and Hemodynamics in Endotoxin-Challenged Patients Methods Mongrel dogs weighing approximately 20–25 kg were fed a low-protein diet for seven days. Animals underwent bilateral nephrectomy and a dialysis catheter (Bard Access Systems, Salt Lake City, Utah, USA) was inserted via external jugular vein into the right atrium. Intravenous vancomycin (Eli Lilly & Co, Indianapolis, Ind., USA) was administered before surgery as antimicrobial prophylaxis. After surgery they were permitted to eat and drink ad libitum for forty-eight hours. Blood samples for electrolytes and complete blood counts were obtained before the low-protein diet, before surgery, and on postoperative days 1 and 2. The animals were sedated with thiopental sodium (Abbot Laboratories, North Chicago, Ill. USA), intubated and isofluorane (Baxter Healthcare, Deerfield, Ill., USA) general anesthesia was administered via endotracheal tube. An esophageal thermometer was inserted and temperature monitored. An arterial catheter (Arrow International, Reading, Penn., USA), a venous catheter (Diag, Minnetonka, Minn., USA), and a Swan-Ganz thermodilution cardiac output catheter (Argon Medical, Athens, Tex., USA) were placed and transduced. Arterial, central venous, and pulmonary artery waveforms, as well as pulmonary capillary wedge pressure (PCWP) were measured (Model Viridia 24C, Hewlett-Packard GmbH, Boblinge Germany) before institution of continuous venovenous hemofiltration (CVVH) and at hourly intervals afterwards. Cardiac outputs were measured by thermodilution (Model COM-1, American Hospital Supply, Irvine, Calif., USA) before CVVH and at hourly intervals thereafter. CVVH was interrupted and the dialysis lines clamped during cardiac output and PCWP measurements. Blood pressure, pulse, and temperature were recorded at fifteen minute intervals. Blood aliquots were obtained at 0, 1, 4, 5, 7 and 9 hours for electrolytes, complete blood counts, and cytokine measurements.

After all access lines were secured in the animal and baseline parameters and laboratory studies obtained, conventional continuous venovenous hemofiltration was instituted for one hour (Gambro AK-10, Gambro Lundia AB, Sundsvall, Sweden) with an F-40 hollow-fiber dialyzer, (Fresenius, Walnut Creek, Calif. USA). Extracorporeal blood flow was regulated at 120 ml/min. Ultrafiltrate production was monitored and a balanced electrolyte replacement solution was infused on a 1:1 volume replacement basis.

After the first hour, a RAD containing porcine proximal tubule cells (Cell RAD), or an otherwise identically treated hollow-fiber dialyzer without proximal tubule cells (Sham RAD) was introduced as depicted in FIG. 1. RAD fabrication is described in detail elsewhere. [Refs. 18, 19, 20, all of which are incorporated herein by reference.] Fourteen ml/min of ultrafiltrate from the hemofilter was directed into the luminal space of the RAD, and thus into direct contact with cultured porcine proximal tubule cells or laminin treated polysulfone hemodialysis membranes, in the Cell RADs and the Sham RADs, respectively. Of the 120 ml/minute blood flow through the hemofilter, 80 ml/minute of post-hemofilter blood was directed into the extraluminal space of the RAD, as shown in FIG. 1. Transmural and hydraulic pressure gradients in the RAD were adjusted to maintain a reabsorption rate of 7 ml/minute of ultrafiltrate into the post-hemofilter extracapillary blood compartment. Previous work has demonstrated that such reabsorption takes place by both trans- and para-cellular pathways in the Cell RAD. [Ref. 18]

After the initial hour of hemofiltration and three hours of treatment with the RAD, lipopolysaccharide 2.0 mg/kg (L-2880, Sigma, St. Louis, Mo., USA), was infused intravenously over one hour. This protocol was selected due to its similarity to the cardiovascular derangement seen in endotoxin shock of human patients. As described in other studies, a decline in an animals' mean arterial pressure was treated with infusions of normal saline and, in the first animals tested, by infusions of dopamine hydrochloride (Elkins-Sinn, Cherry Hill, N.J., USA). Analysis of the first few animals suggested that even large dopamine infusions did not restore blood pressure independent of volume resuscitation, so dopamine infusions were not used in subsequent animals. Two animals in the cell RAD group and four in the sham RAD group received dopamine. Four hours after the conclusion of the lipopolysaccharide infusion, the animals were euthanized.

Assays

Arterial blood gases were measured with an ABL Series 500 (Radiometer Medical A/S, Copenhagen, Denmark). Serum electrolytes were measured with an automated chemical analyzer (Synchron CX-7, Beckman Instruments, Brea, Calif., USA). Complete blood counts were performed on an automated counter (Coulter Gen-S, Coulter, Hialeah, Fla., USA), and differential counts were performed by hand.

IL-10 and TNF-$\alpha$ levels in the serum samples were evaluated in triplicate by ELISA. Anti-human IL-10 and anti-human TNF-$\alpha$ antibodies, the kind gift of Dr. Robert Streiter (University of Michigan, Ann Arbor Mich., USA), showed a strong cross species affinity with cytokines produced by both porcine and canine LPS stimulated monocytes in culture. Comparison of serum levels to human recombinant IL-10 and TNF$\alpha$ standards (R&D Systems Minneapolis, Minn., USA) resulted in a qualitative assessment of the systemic IL-10 and TNF-$\alpha$ being produced by both the animal and the RAD.

Ultrafiltrate ammonia levels were assayed with a commercially available kit (Sigma Diagnostics, St. Louis, Mo., USA).

Statistics

It was noted in the first animals that the experimental animals, like human patients, had a spectrum of initial (t=0) systolic (range, 111–174 mm Hg) and diastolic pressures (range, 66–118 mm Hg).

Clinically relevant parameter, percentage drop in MAP was used as the outcome measure. This selection allows the use of a continuous variable, but one less sensitive to inter-subject variability than the raw pressure data alone. The hemodynamic data were gathered as systolic and diastolic pressures, in mmHg, and converted to MAP by the formula MAP=SBP=3+2/×DBP/3. The data were then normalized to the t–4 hour time point, immediately prior to the one hour endotoxin infusion, so that pressures were expressed as a percentage of the pre-endotoxin values. Hemodynamic data were analyzed by repeated-measures analysis of variance (ANOVA) over all post-infusion time points. Cytokine peak levels were compared between cell and sham RAD animals with one-way ANOVA. Ammonia excretion between groups was compared with Welch's t test. Categorical variables were compared with Fisher's Exact Test. Statistical analysis was performed using the Stata software package (Stata 6 for Unix, Stata Corporation, College Station, Tex.).

Results

Characteristics of the experimental animals are listed in Tables 1 and Table 2. All animals were uremic to a similar extent.

Hemodynamics

Figure 2:
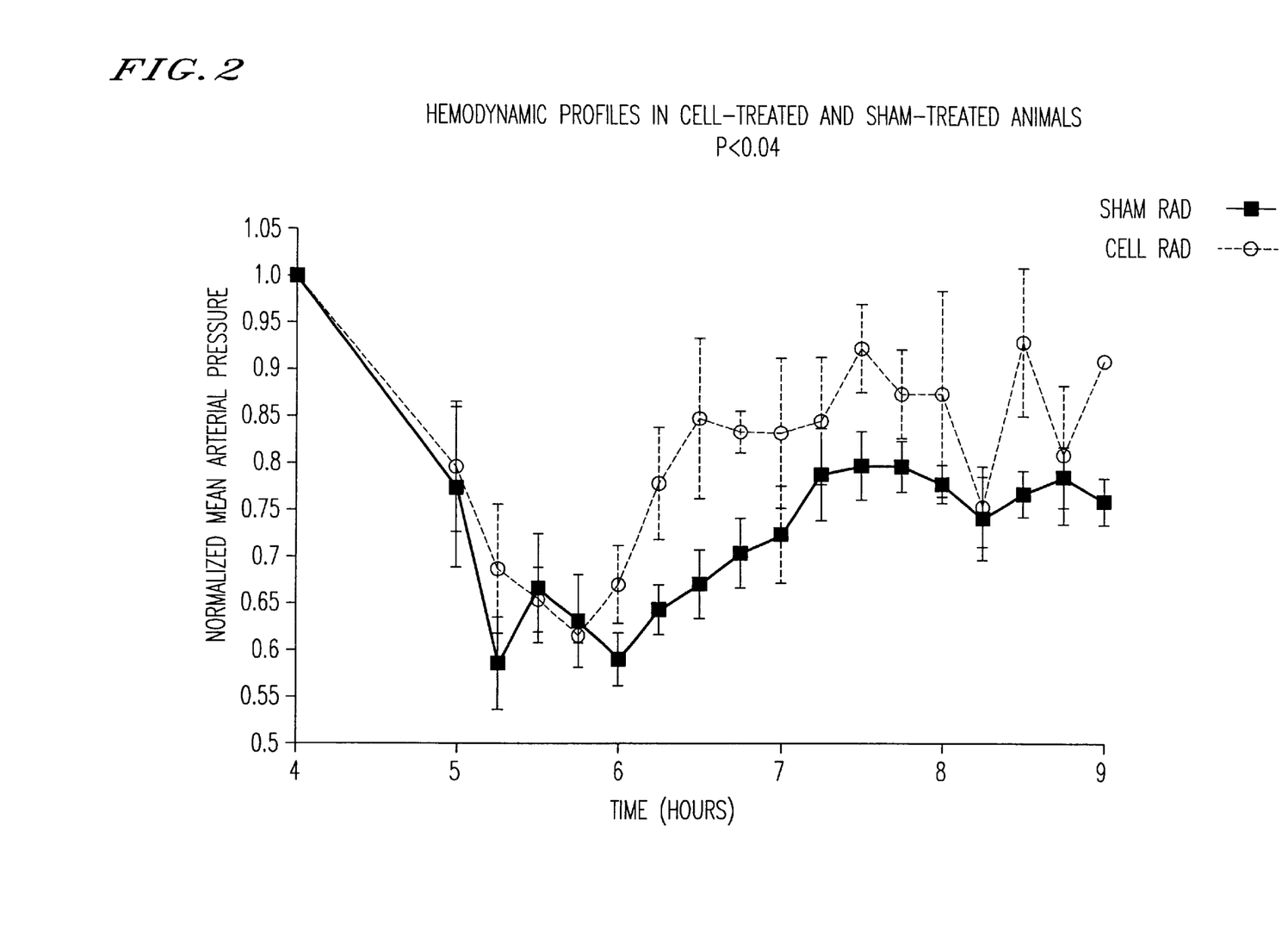
FIG. 2: Mean arterial pressure in LPS-challenged dogs

All animals displayed a rapid decrease in MAP after administration of lipopolysaccharide followed by slow recovery toward baseline. Pre-endotoxin mean arterial pressures in the animals ranged from 46 mm Hg to 125 mm Hg. This heterogeneity may be due to differences in volume status, which is likely as PCWPs ranged from six to thirteen mm Hg, individual reactions to the hemofilter, or may merely reflect the heterogeneous population of mongrel dogs used in the experiments. FIG. 2 shows the mean arterial pressure normalized to the pre-LPS time point in cell RAD (n=5) and sham RAD (n=5) animals.

Repeated measures analysis of variance (ANOVA) for mean arterial pressure demonstrated statistically significant differences in MAP between cell RAD and sham RAD treated animals, although individual time points only demonstrated a trend towards significance.

Cytokines

Figure 3:
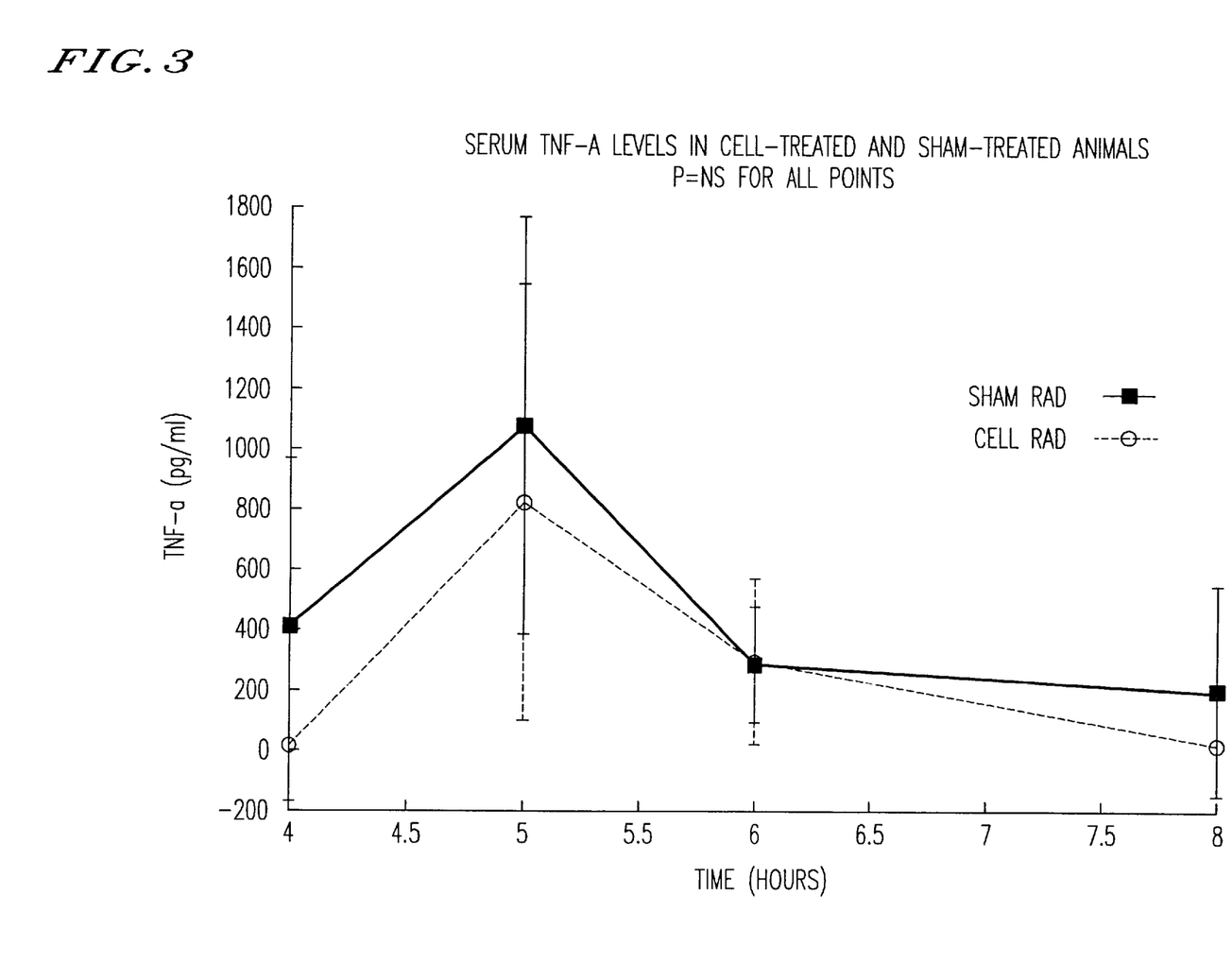
FIG. 3: TNF-α levels in LPS-challenged dogs

Serum TNF-$\alpha$ levels rose after LPS administration, and returned to near-baseline levels after four hours (FIG. 3). Although TNF-$\alpha$ levels were on average lower in cell RAD treated animals versus sham-treated animals, the difference was not statistically significant.

Figure 4:
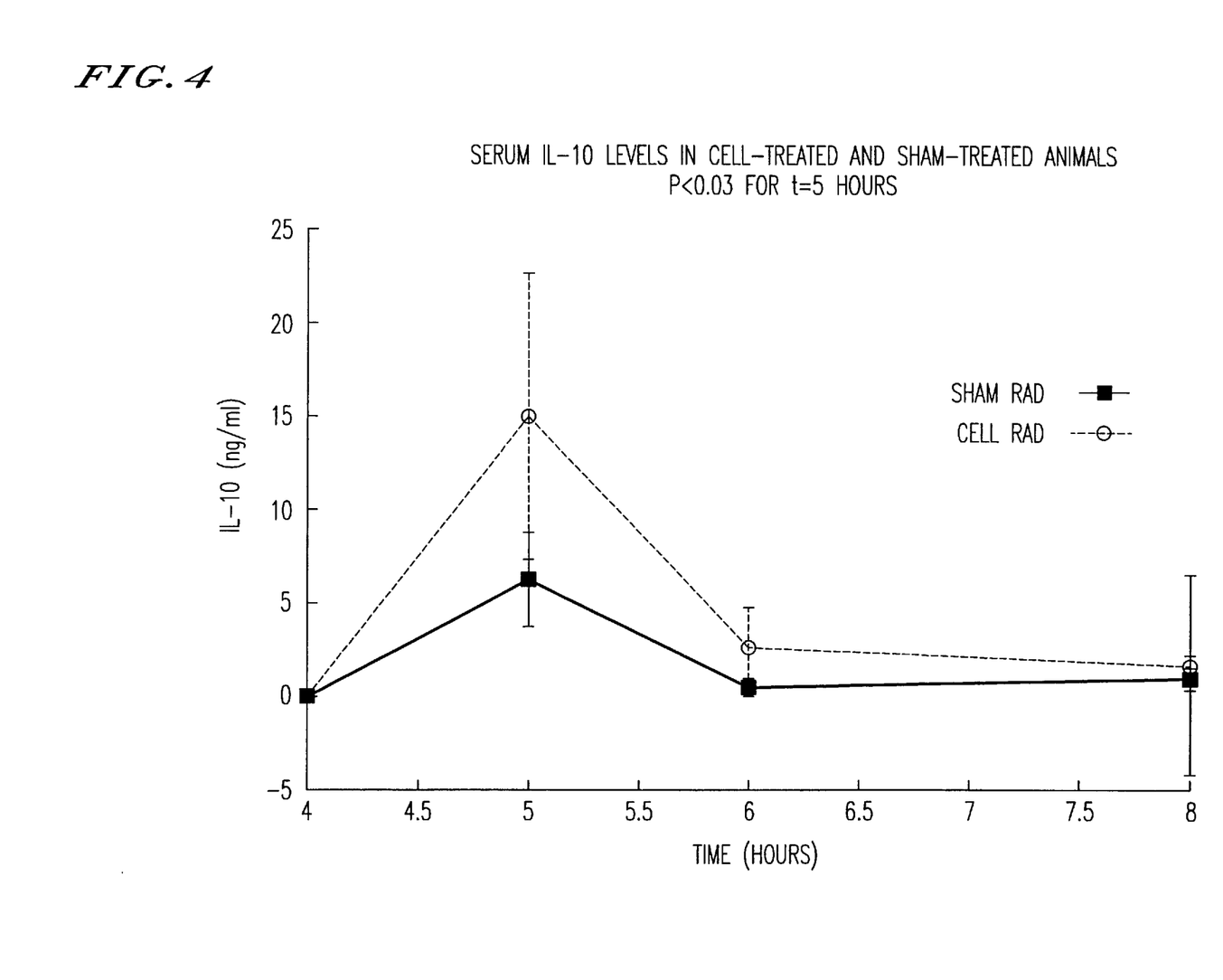
FIG. 4: IL-10 levels in LPS-challenged dogs

Serum IL-10 levels also rose sharply after lipopolysaccharide infusion, with cell-treated animals achieving significantly higher peak IL-10 levels than sham-treated animals (FIG. 4). Of note, IL-10 levels in cell-treated animals were not significantly different from levels observed in a comparable set of non-nephrectomized mongrel dogs stressed with the same protocol (data not shown).

Proximal Tubule Cell Viability

In the endotoxin model of septic shock described above, ammoniagenesis by the RAD was measured as a marker of cellular viability and metabolic function while it was in the extracorporeal circuit. Unfortunately, some interference with our assays in the dopamine treated animals was needed. Data pooled from animals in this study which had not received dopamine (five animals), as well as animals treated similarly but rejected for analysis here due to protocol violations (one animal), incomplete data collection (one animal) or evidence of antecedent illness (two animals), demonstrate metabolic activity in the RAD under conditions of endotoxin stress. Ammonium (NH+4) production averaged 0.56±5.1 $\mu$mol/hour in sham-treated animals, versus 14.4±10.4 $\mu$mol/hour in Cell RAD treated animals (P<0:005, Welch's t test).

TABLE 1

Characteristics of Experimental Animals

|  | Cell RAD | Sham RAD | P-value |
| --- | --- | --- | --- |
| N | 5 | 5 |  |
| Weight (kg) (Mean ± SD) | 24.16 ± 2.8 | 20.7 ± 2.1 | 0.06 |
| Initial WBC (Mean ± SD) | 7.75 ± 4.21 | 12.5 ± 4.8 | 0.16 |
| Initial MAP (Mean ± SD) | 115.9 ± 19.3 | 105.2 ± 20.2 | 0.42 |
| Initial Heart Rate (Mean ± 4SD) | 121 ± 2.7 | 114 ± 18.4 | 0.65 |

TABLE 2

Serum Values in RAD-Treated and Sham-Treated Dogs

|  | Sodium (mEq/L) | Potassium (mEq/L) | Chloride (mEq/L) | Bicarbonate (mEq/L) | BUN[α] (mg/dL) | Creatinine (mg/dL) | Glucose (mg/dL) | Calcium (mEq/L) | Phosphorous (mEq/L) |
|---|---|---|---|---|---|---|---|---|---|
| Sham-Treated (N = 5) | | | | | | | | | |
| Pre-Experiment | 140 ± 3.8 | 6.8 ± 0.6 | 108 ± 2.3 | 16 ± 1.5 | 89 ± 13 | 8.9 ± 0.6 | 186 ± 54 | 13.7 ± 1.5 | 9.6 ± 1.2 |
| Post-Experiment | 147 ± 4.8 | 4.6 ± 1.4 | 120 ± 7.9 | 16 ± 2.4 | 67 ± 7.3 | 6.8 ± 0.4 | 116 ± 37 | 10.1 ± 1.1 | 7.4 ± 1.5 |
| RAD-Treated (N = 5) | | | | | | | | | |
| Pre-Experiment | 142 ± 2 | 6.8 ± 1.7 | 109 ± 2.3 | 17 ± 1.2 | 98 ± 37.6 | 9.3 ± 1.6 | 196 ± 60 | 13.3 ± 0.8 | 8.5 ± 1.5 |
| Post-Experiment | 146 ± 3.3 | 4.3 ± 1.1 | 118 ± 4.4 | 17 ± 1.5 | 78 ± 31.9 | 7.4 ± 1.4 | 92.1 ± 73.6 | 10.6 ± 0.8 | 6.6 ± 1.4 |

[α]P > 0.63 Sham RAD versus Cell RAD

TABLE 3

Peak Cytokine Levels in LPS-Challenged Dogs (Mean ± SD)

|  | Cell RAD | Sham RAD | P-value |
|---|---|---|---|
| TNF-α (pg/ml) | 784 ± 805 | 1080 ± 693 | 0.551 |
| IL-10 (ng/ml) | 16.1 ± 7.92 | 6.27 ± 2.46 | 0.029 |

Example 2

Treatment of a Human Patient Afflicted with Sepsis with Renal Tubule Cells

A 29 year-old man presented to the emergency room with a one-day history of nausea, vomiting, diarrhea, chills and fever. The morning of admission he noted redness, swelling and pain in his right thigh. Over the subsequent four hours the redness, swelling and pain extended to his calf. Upon presentation, the patient had a temperature of 103.5° F., and blood pressure of 101/42. Bibasilar rates were noted. His right thigh and calf were erythematous, swollen and tender. On admission, his white blood count was 20,200 with a marked left shift, and his platelet count was 174,000. His serum electrolytes were normal, but his serum creatinine was 2.9 mg/dl and BUN 38 mg/dl. His arterial blood gases on 3L nasal cannula was pH 7.46 pCO$_2$32 mm Hg, pO$_2$65 mm Hg. Chest x-ray showed no infiltrates. Blood cultures were obtained, ceftriaxone 2 gm and clindamycin 900 mg were given intravenously. A CT scan of his right leg revealed no gas, fluid collections or necrotizing tissue.

After slight improvement over the first 24 hours, his condition began to rapidly deteriorate with shortness of breath, oliguria, and hypotension. Repeat plasma chemistry values revealed rising liver function tests with ALT 155 IU/ml, AST 189 IU/ml total bilirubin 4.1 mg/dl serum creatinine 7.6 mg/dl, BUN 69 mg/dl, calcium 6.8 mg/dl and a creatinine phosphokinase 460 IU/ml. Arterial blood gases on 6L nasal cannula were pH 7.23, pCO$_2$40 mm Hg, pO$_2$68 mm Hg. Chest x-ray revealed multilobar infiltrates. A clinical diagnosis of streptococcal toxic shock syndrome was made and intravenous antibiotics, were continued with ceftriaxone 2 gm q8h, clindamycin 900 mg q8h and a single dose at vancomycin 1.5 gm. He was transferred to the intensive care unit approximately 24 hours after admission and intubated to maintain adequate oxygenation with a pO$_2$ of 68 mm Hg at a Fi O$_2$ of 60 percent. His blood cultures were reported positive for beta hemolytic streptococcus Group A. Emergent surgical exploration of his left calf revealed no necrotizing fasciitis or myonecrosis, which was confirmed on histologic evaluation. Tissue specimens from the procedure were also culture positive for beta-hemolytic streptococcus Group A.

After returning from surgery, now 36 hours after admission, his condition continued to deteriorate with worsening hypotension to 68/42 requiring vasopressor support with dopamine, phenylephrine, and levarterenol. He was started on continuous venovenous hemofiltration to treat his acute renal failure. Over the subsequent 72 hours, his liver function tests elevated to a high of ALT 904, AST 1404, total bilirubin 5.6 mg/dl, creatinine phosphokinase 45, 530, and lows of serum calcium 5.9 mg/dl, serum albumin 1.8 mg/dl, hematocrit 29.5 percent, platelet count 28,000. During this critical period, his cardiac output was markedly elevated between 9–12 L/min and his systemic vascular resistance varied between 300–500.

Because of his worsening condition, the patient was considered to be included in a Phase I/II clinical trial at The University of Michigan to test the safety and functionality of a bioartificial kidney. Pre-clinical large animal experiments have suggested that this device can ameliorate the cardiovascular consequences of septic shock. This study is an investigator-initiated trial reviewed and approved by the U.S. Food and Drug Administration (FDA) and by the local institutional review board (IRB). The patient met all inclusion and exclusion criteria of the protocol and his family agreed to allow him to participate in the study and signed a detailed informed consent document.

The bioartificial kidney is comprised at a continuous venovenous hemofiltration (CVVH) circuit connected to a synthetic hemofiltration cartridge (Fresenius F40, Fresenius AG, Bad Hamburg, Germany), and a Renal Tubule Assist Device (RAD). The RAD is a commercial hemofiltration cartridge (F40) in which human renal tubule cells have been grown to confluence along the inner surface of the hollow fibers. The human cells were isolated and expanded from human kidneys obtained from the National Disease Research Interchange (NDRI, Arlington, Va., USA). NDRI is a not-for-profit organization and provides tissues and organs originally retrieved for transplant, but due to donor/recipient incompatibility, transplantation is not possible. A written informed consent document was obtained for each kidney donor and is kept on file at the tissue acquisition site.

After 36 hours of CVVH, the bioartificial kidney replaced the hemofiltration cartridge in the extracorporeal circuit. A variety of physiologic parameters of the patient were carefully monitored prior to, during, and after the use of the biohybrid device. Key parameters are summarized in FIGS. 5–7.

Figure 5:
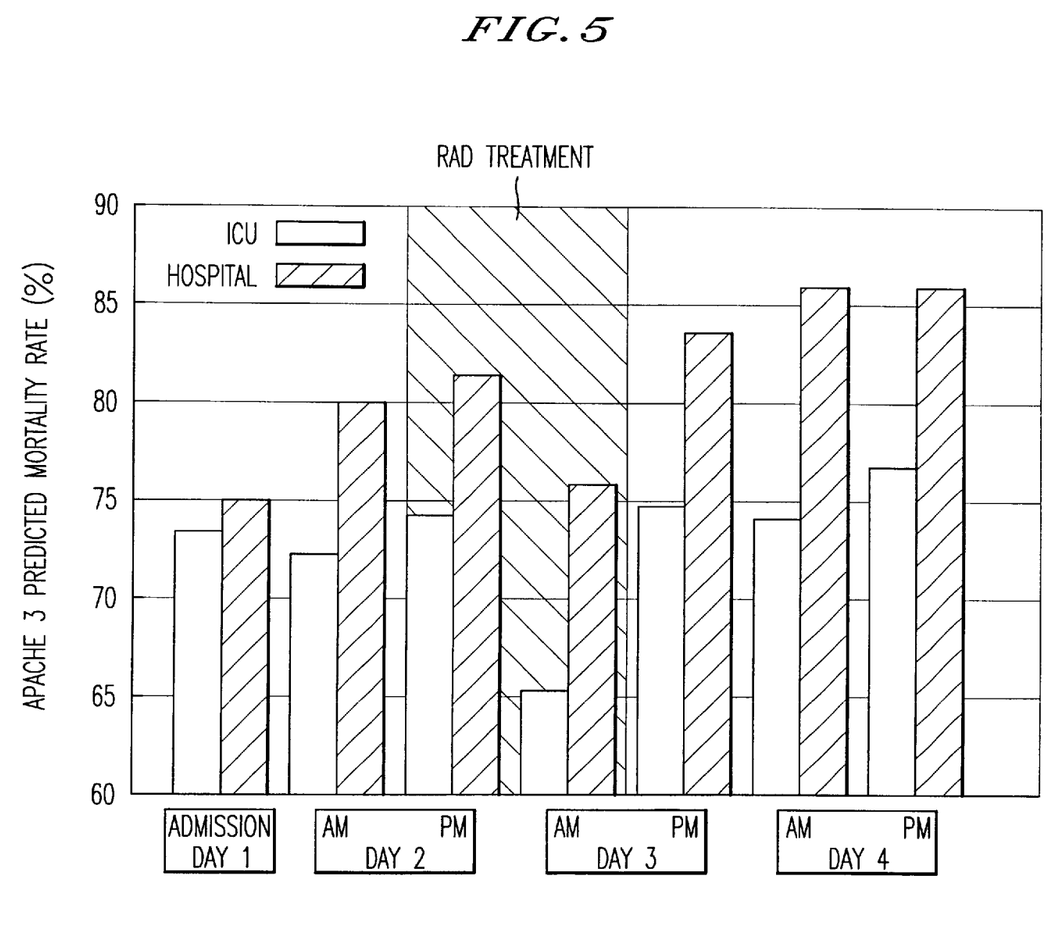
FIG. 5: Patient's predicted mortality rates from daily apache 3 scoring in the medical ICU. The AM rate is an 8 AM Apache 3 score using the parameters of the patient at that hour of the day. The PM rate is determined by compiling the worst score in each parameter during the patient's 24 hour ICU stay from midnight (0000 hours) the preceding day to the following midnight (2359 hours)

As displayed in FIG. 5, the patient's Apache 3 score and predicted ICU and in hospital mortality rate was dramatically reduced during RAD treatment. The AM score was assessed after 16 hours of RAD therapy. These predicted mortality rates during RAD treatment were substantially lower, compared to the prior and following day (AM and PM) values. The RAD was discontinued after 21.5 hours of use due to a prior determined termination event of a platelet count lower than 35,000 for safety reasons.

Figure 6:
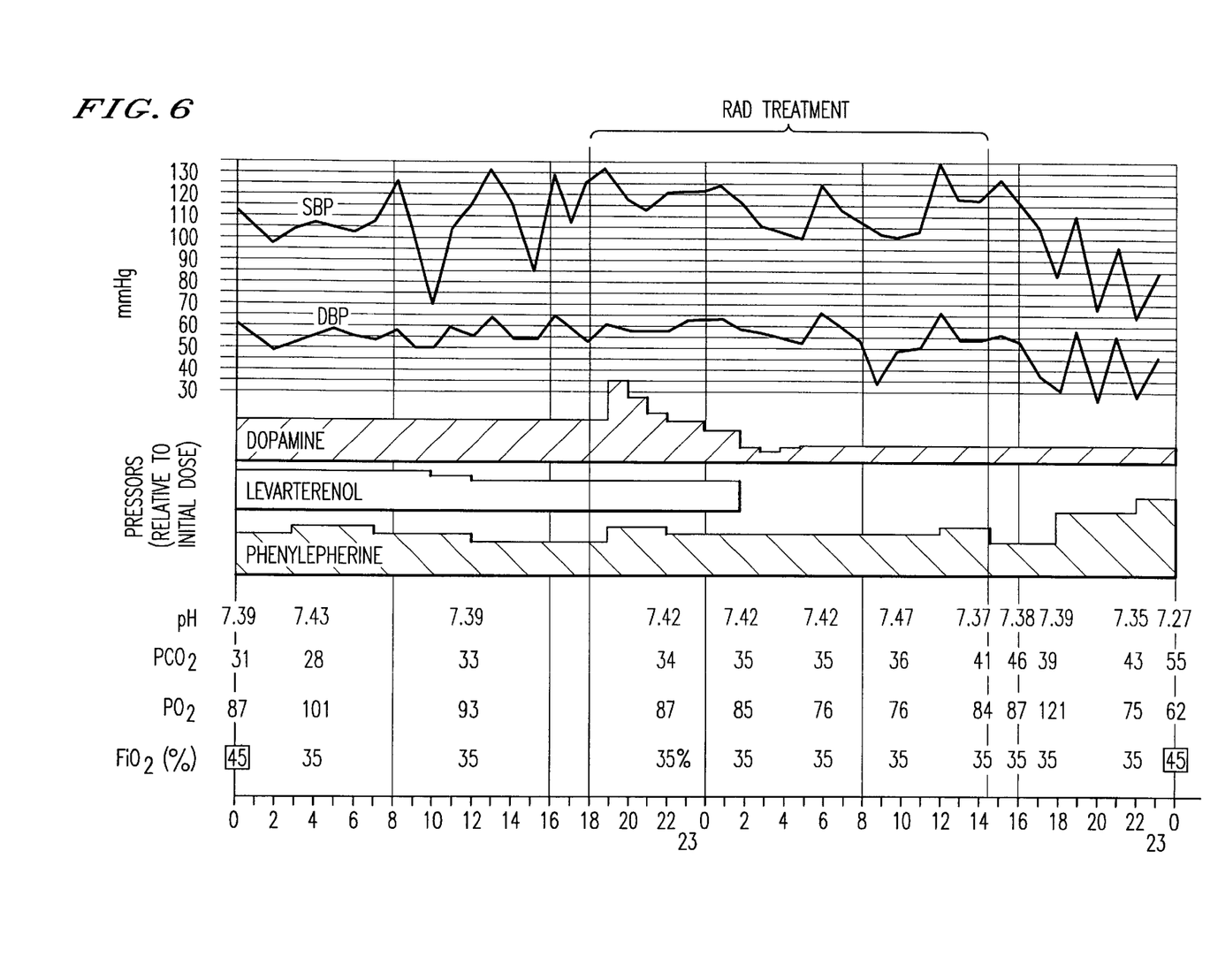
FIG. 6: Blood pressures, vasopressor dosage and arterial blood gases in relation to fractional inspired oxygen ($F_i O_2$) with time in the patient. The vasopressor dosage is presented as relative to the dose at the beginning (midnight, hour 0) of the time period. The beginning 5 dosages were the following: dopamine (5 ug/kg/min), phenylepherine (1.5 ug/kg/min) and levarterenol (0.2 ug/kg/min)
Figure 7:
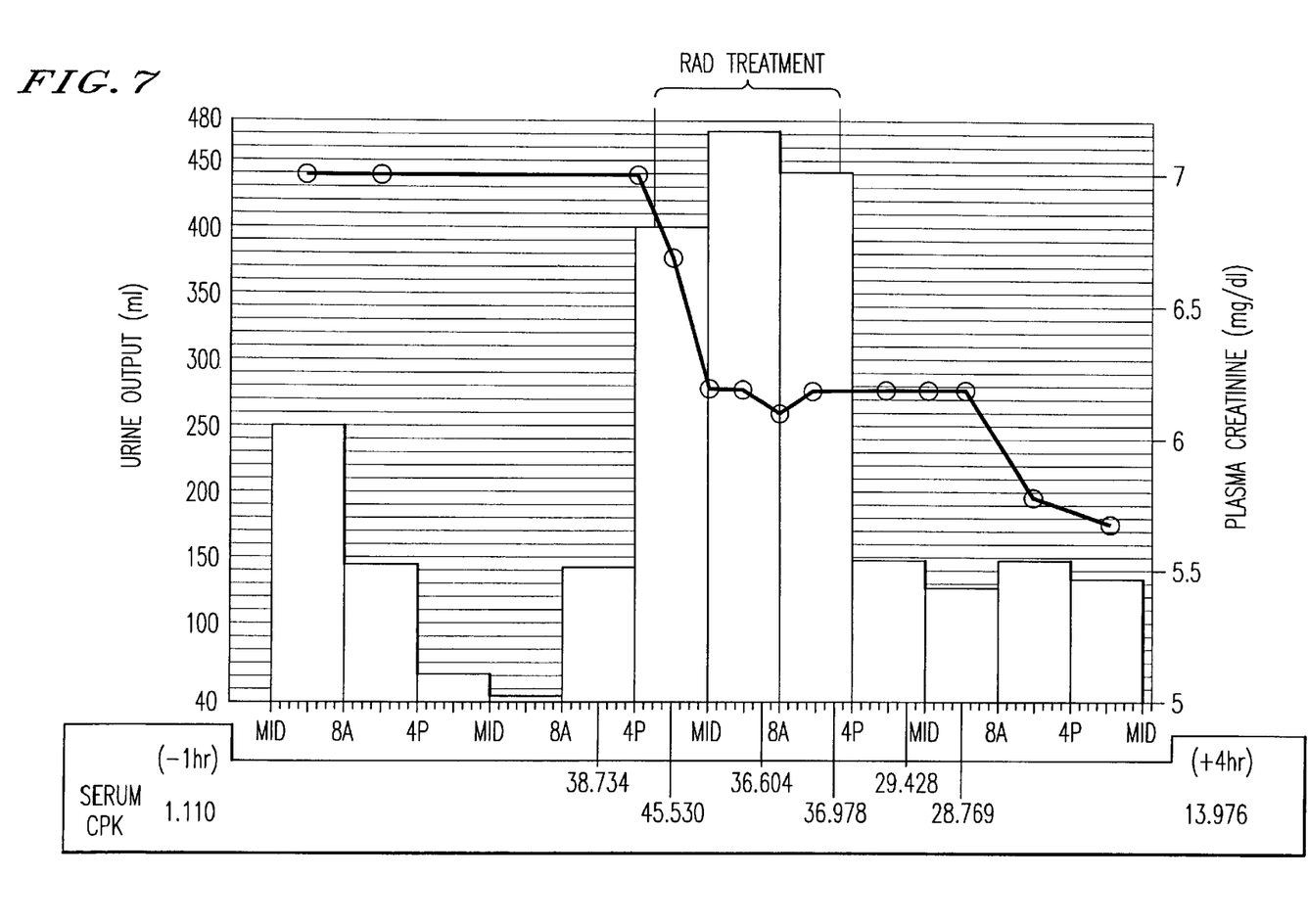
FIG. 7: The time course of urine output (left scale) and plasma creatinine concentration (right scale) in this patient. The plasma CPK levels (I.U./ml) are also displayed along the bottom panel.
Figure 8A:
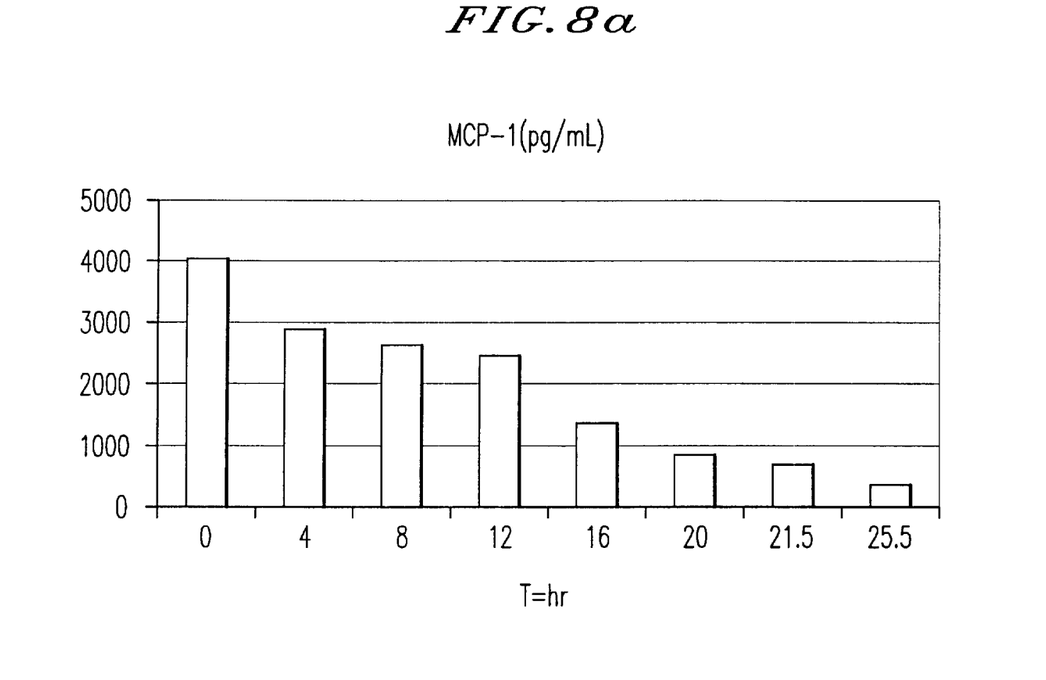
FIG. 8: Cytokine levels observed in the treatment described in Example 2 below. (A) MCP-1 levels (pg/ml); (B) G-CSF levels (pg/ml); (C) IL-1 β (pg/ml); and (D) IL-1 ra (pg/ml).
Figure 8B:
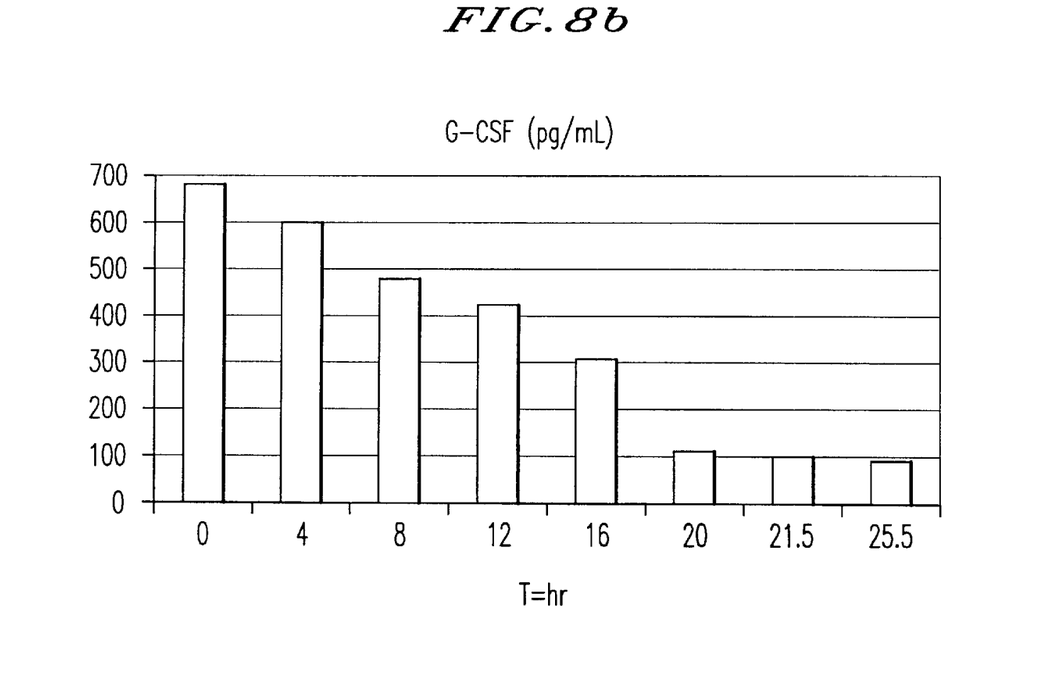
Figure 8C:
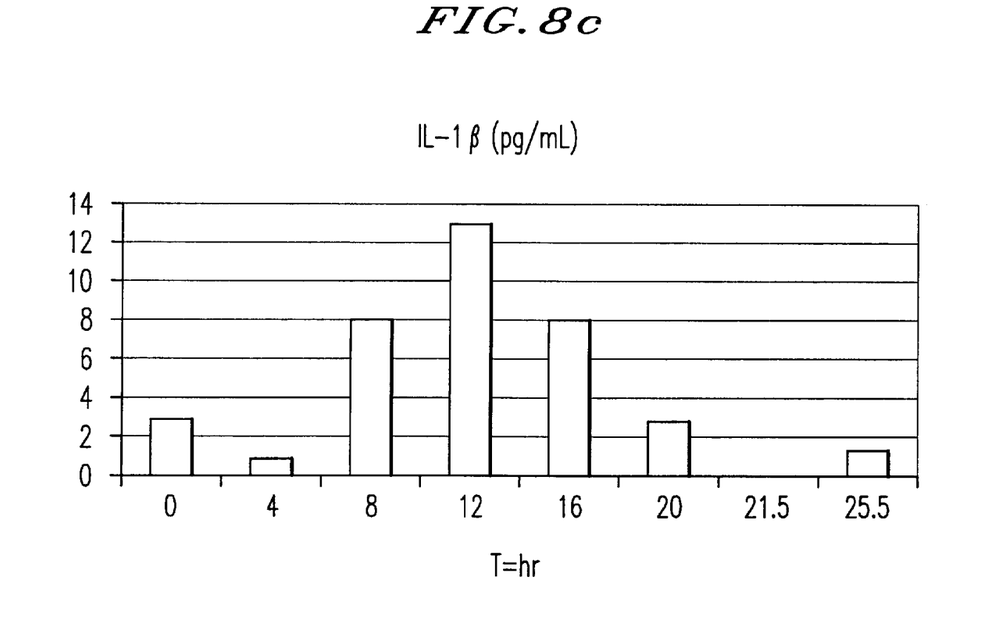
Figure 8D:
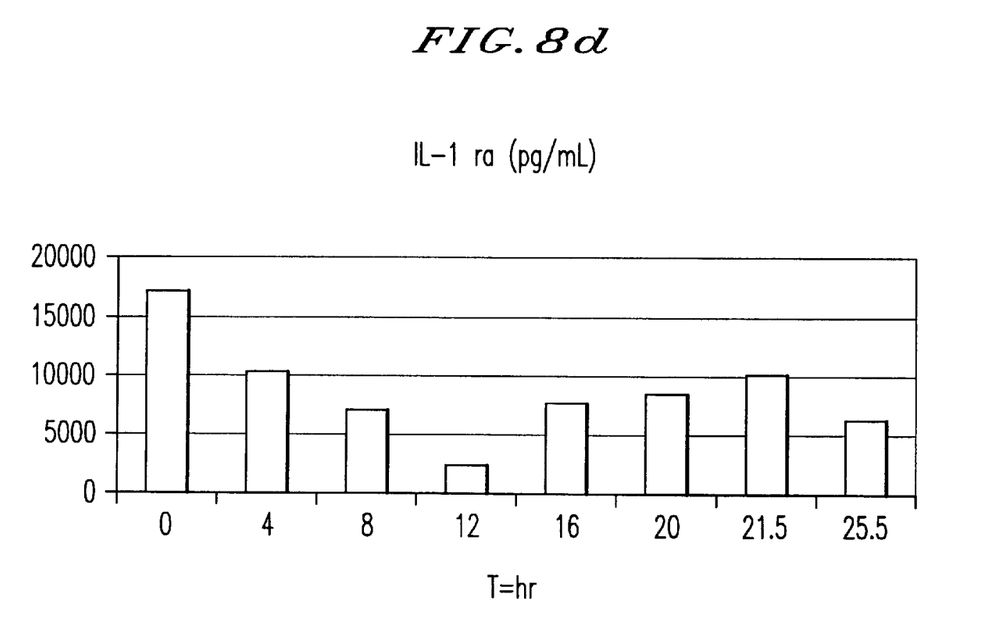

Key physiologic parameters, which contributed to the improved Apache 3 predicted mortality rates are summarized in FIGS. 6 and 7. In FIG. 6, the systolic and diastolic blood pressures in relation to the vasopressor requirements are detailed along with key respiratory parameters. The patient's blood pressure was much more stable during RAD therapy and his pressor requirements markedly diminished during the treatment period. The increase in dopamine dosage as the RAD was placed in the circuit was required to maintain blood pressure during the initial phases of extracorporeal exposure to the RAD, a phenomena observed in preclinical studies and in other synthetic extracorporeal cartridges during first exposure to the patient. Within 4 to 10 hours following discontinuation of RAD therapy, the pressor requirements of the patient increased and his respiratory parameters worsened.

The effect on renal function was also striking. As seen in FIG. 7, RAD therapy had a time correlation to convert an oliguric acute renal failure state to a non-oliguric state. This improved urine flow was reflective of enhanced renal clearance function. The creatinine clearances changed from 4.9±0.9 ml/min to 10.9±0.6 ml/min, and 6.2±0.9 ml/min, prior to, during, and after therapy, respectively.

In addition, the 21.5 hours of treatment coincided with a reduction in plasma creatinine concentrations from 7.0 to 6.0 mg/dl despite substantial ongoing rhabdomyolysis as reflected with the elevated CPKs during this treatment interval. In fact, both plasma and urine myoglobin levels were greater than 100,000 units/ml during this treatment period.

The RAD also demonstrated maintenance of excellent viability and functionality during the treatment period. Cell counts over the treatment interval of renal tubule cells exiting the RAD in the processed ultrafiltrate was cumulatively less than 0.1% of the total renal epithelial cell number (approximately $1.0 \times 10^9$ cells) within the device. This viability was despite a critically ill uremic individual with toxic shock syndrome and marked myoglobinuria. The functionality of tubular cell function was demonstrated by the tubular fluid/ultrafiltrate glutathione (GSH) ratios of 0.80. GSH reclamation is dependent upon active breakdown and transport of amino acids by the tubule cells. Plasma 1.25—dihydroxy—vitamin $D_3$ levels also improved during the treatment interval from 15 to 22 pg/ml, demonstrating endocrinologic activity of the cells.

Fortunately for the patient, despite an Apache 3, score predicting as high as a 92 percent in hospital mortality rate, he eventually improved with his liver function tests returning to normal, respiratory parameters improving with successful extubation, and a return in renal function, so that hemofiltration and hemodialysis was discontinued. He was discharged from the ICU after 10 days and the acute care hospital after 15 days.

In addition, plasma cytokine levels were measured prior to, during, and after RAD therapy in this patient. As demonstrated in Table 4 and FIG. 8, the RAD was associated with a decline in several pro-inflammatory cytokine levels and an increase in anti-inflammatory cytokine levels during toxic shock.

TABLE 4

Plasma Levels of Inflammatory Proteins with RAD Therapy

| Protein | Normal Range | Time (hours) | | | | | | | |
|---|---|---|---|---|---|---|---|---|---|
| | | 0 | 4 | 8 | 12 | 16 | 20 | 21.5 | 25.5 |
| TNF-α (pg/ml) | <15.6 | 20 | 20 | 21 | 19 | 14 | 14 | 11 | 15 |
| STNFRI (pg/ml) | 500–2000 | 24,101 | 24,769 | 25,056 | 28,445 | 25,470 | 22,828 | — | 27,188 |
| STNFRII (pg/ml) | 950–2500 | 50,869 | 53,150 | 47,518 | — | 51,139 | 49,091 | — | 44,175 |
| IL-1β (pg/ml) | <3.9 | 3 | 1 | 8 | 13 | 8 | 3 | 0 | 1.5 |
| IL-1ra (pg/ml) | 50–1400 | 17,119 | 10,364 | 7,237 | 2,508 | 7,948 | 8,710 | 10,248 | 6,441 |
| IL-1sRII (ng/ml) | 2–9 | 103 | 105 | 94 | 86 | — | — | 95 | 81 |
| IFN-• (pg/ml) | <15.6 | 42 | 65 | 35 | — | 49 | 26 | — | 5 |
| IL-6 (pg/ml) | <3.13 | 833 | 736 | 853 | — | 1,255 | 784 | — | 932 |
| IL-8 (pg/ml) | <31.2 | 152 | 141 | 132 | 134 | — | — | 140 | 74 |
| MCP-1 (pg/ml) | 113–340 | 4,061 | 2,886 | 2,614 | 2,448 | 1,343 | 816 | 671 | 343 |
| MIP-1• (pg/ml) | <46.9 | <46.9 | <46.9 | <46.9 | <46.9 | — | — | <46.9 | <46.9 |
| IL-10 (pg/ml) | <7.8 | 9 | 5 | 2 | — | 2 | 5 | — | 5 |
| IL-13 (pg/ml) | <62.5 | <125 | <125 | <125 | <125 | — | — | — | <125 |
| G-CSF (pg/ml) | <39 | 684 | 598 | 485 | 435 | 307 | 114 | 104 | 90 |

TABLE 4-continued

Plasma Levels of Inflammatory Proteins with RAD Therapy

| Protein | Normal Range | Time (hours) | | | | | | | |
|---|---|---|---|---|---|---|---|---|---|
| | | 0 | 4 | 8 | 12 | 16 | 20 | 21.5 | 25.5 |
| GM-CSF (pg/ml) | <7.8 | <7.8 | <7.8 | <7.8 | <7.8 | <7.8 | — | — | <7.8 |
| CRP (ng/ml) | <2,000 | 650,000 | 610,000 | 865,000 | 734,000 | — | 745,000 | — | 705,000 |

*Footnotes for TABLE 4
Hours refer to 0 = pre-therapy; 4, 8, 12, 16, 20 of RAD therapy; 21.5 h just prior to treatment discontinuation; 25.5 h is 4 hours post therapy.
Blanks identity measurements not done due to sample size limitations.
Normal values are derived from diagnostic kits.
Abbreviations: TNF (tumor necrosis factor)-•; STNFR (soluble TNF receptor)-I, II; IL (Interleukin-1β; IL-1ra (receptor antagonist); IL-1sR (soluble receptor)-II; IFN (interferon)-•; MCP (monocyte chemoattractant Protein)-1; MIP (macrophage migratory inhibitory factor)-1•1 G (granulocyte)-CSF (colony stimulating factor); GM (Macrophage) CSF; CRP (C-Reactive Protein).

Example 3

Porcine Proximal Tubule Culture on Microcarriers

Studies were performed to assess the feasibility of amplifying porcine proximal tubule cells in suspension culture using microcarrier beads in comparison to a protocol in which the cell amplification occurs on conventional two-dimensional polystyrene culture dishes. Microcarrier cultures were kept in suspension using a magnetic stirring system (Techne, Model MCS-104L, Princeton, N.J.). After a few preliminary studies in 100 mL and 250 mL culture volumes using glass, polystyrene, gelatin and dextran microcarriers from various vendors, we decided to focus on two types of microcarriers, microporous gelatin (Cultisphere G, Hyclone, Logan, Utah) and collagen coated dextran (Cytodex 3, Pharmacia Biotech, Uppsala, Sweeden) as these two types of microcarriers showed the fastest growth and highest yield as assessed by cell numbers. One liter spinner flasks were used for all future cultures to allow for the cell numbers necessary for RAD seeding.

Both types of microcarriers arrived in a desiccated state and were rehydrated and rinsed with phosphate buffered saline. Prior to seeding with cells, the microcarriers were sterilized by autoclaving, the PBS was replaced with media and the bead media mixture was allowed to equilibrate in a 37° C., 5% CO2 incubator. Cells were seeded on to the microcarriers as follows. First porcine proximal tubule cells at second pass were trypsinized from two dimensional culture plates, centrifuged and resuspended in growth media. This slurry was then added to the spinner flask. For porcine proximal tubule cells, the stir plate settings were adjusted to intermittent stirring, one minute on and one hour off for a total of 4 cycles. The media was changed at the end of the four cycles to remove all unattached cells and the spinner console settings adjusted to continuous stirring at a speed just fast enough to keep the microcarrier-cell aggregates in suspension (around 20 rpm). Because of the nutrient and oxygen requirements of these dense cultures, media was changed daily. A representative sample was taken from the flask every few days for analysis of lactate and cell growth as determined by direct cell counts. After two weeks in culture, microcarriers with cells could be loaded into a cell cartridge or cells removed from the microcarriers for cell seeding.

For cell dissociation, the microcarrier-bead aggregates were rinsed with PBS to remove the calcium and magnesium ions that inhibit the trypsiniztion. The PBS was then removed and replaced with trypsin. The slurry was incubated at 37° C. for 20 minutes to allow for the detachment of the cells from the dextran microcarriers. Soybean trypsin inhibitor was added to the flasks and the beads separated from the cells by differential sieving if necessary. The gelatin microcarriers completely dissolved in trypsin and thus did not need to be sieved. Cells were then counted, centrifuged and resuspended in growth media. The cell concentration for seeding was calculated by using the surface area, actual lumen volume of the RAD and the cell number per surface area of the cells in two dimensional culture. For example, a RAD created from a Fresenius F-40 has a surface area of 7000 $cm^2$ and an actual lumen volume of 35 mL, therefore A the cell concentration would be 7000 $cm^2$/35 mL×$10^7$ cells/57 $cm^2$=3.5×$10^7$ cells/mL. The total cell number was calculated by multiplying the cell concentration by the actual lumen fill volume and then multiplying again by four seedings. It is important to note that the seeding concentrations used at this time were calculated for a 1X seeding as calculated by surface area. A ¼ X seeding ratio could also be used.

Obviously, numerous modifications and variations of the present invention are possible in light of the above teachings. It is therefore to be understood that within the scope of the appended claims, the invention may be practiced otherwise than as specifically described herein.

References

[1] Bernard G, Vincent J L, Laterre P F, et al. Efficacy and safety of recombinant human activated protein c for severe sepsis. NEJM 344:699–709, 2001
[2] Kellum J. Immunomodulation in sepsis: the role of hemofiltration. Minerva Anestesiol 65:410–418, 1999
[3] Tran D D, Groenveld A J, van der Meulen J, et al. Age, chronic disease, sepsis, organ system failure, and mortality. Critical Care Medicine 18:474479, 1990
[4] Donnelly S, Robertson C. Mediators, mechanisms and mortality in major trauma. Resuscitation 28:87–92, 1994
[5] Bone R C, Fischer C J, Clemmer T P, et al. A controlled clinical trial of high-dose methylprednisolone in the treatment of severe sepsis and septic shock. NEJM 317:653–8, 1987
[6] Horn K. Evolving strategies in the treatment of sepsis and systemic inflammatory response syndrome (SIRS). QJM 91:265–277, 1998

[7] Pinsky M R, Vincent J L, Deviere J, et al. Serum cytokine levels in human septic shock. Chest 103:565–575, 1993

[8] Marty C, Misset B, Tamion F, et al. Circulating interleukin-8 concentrations in patients with multiple organ failure of septic and nonseptic origin. Critical Care Medicine 22:673–679, 1994

[9] Damas P, Reuter A, Gysen P, et al. Tumor necrosis factor and interleukin-1 serum levels during severe sepsis in humans. Critical Care Medicine 17:975–978, 1989

[10] Dinarello C A. The proinflammatory cytokines interleukin-1 and tumor necrosis factor and the treatment of the septic shock syndrome. The Journal of Infectious Diseases 163:1177–1184, 1991

[11] Calandra T, Baumgartner J D, Grau G E, et al. Prognostic values of tumor necrosis factor/cachectin, interleukin-1, interferon-α, and interferon-γ in the serum of patients with septic shock. The Journal of Infectious Diseases 161:982–987, 1990

[12] Jiang J X, Tian H, Zhu P, et al. Plasma cytokines and endotoxin levels in patients with severe organ injury and their relationship with organ damage. Injury 28:509–513, 1997

[13] Breen D, Bihari D. Acute renal failure as a part of multiple organ failure: The slippery slope of critical illness. Kidney International 53 Suppl 66:S-25-S-33, 1998

[14] Sarnak M, Jaber B. Mortality caused by sepsis in patients with end-stage renal disease compared to the general population. Kidney International 58:1758–1764, 2000

[15] Girndt M, Kohler H, Schiedhelm-Weick E. Production of inter-leukin-6, tumor necrosis factor alpha and interleukin-10 in vitro correlates with the clinical immune defect in chronic hemodial ysis patients. Kidney Int 47:559–565, 1995

[16] Girndt M, Sester U, Sester M, et al. Impaired cellular immune function in patients with end-stage renal failure. Nephrol Dial Transplant 14:2807–2830, 1999

[17] Thomas M, Lloyd-Jones D, Thadhani R, et al. Hypovitaminosis d in medical inpatients. NEJM 338:777–783, 1998

[18] Humes H, MacKay S, Funke A, et al. Tissue engineering of a bioartificial renal tubule assist device: In vitro transport and metabolic characteristics. Kidney Int 55:2502–2514, 1999

[19] Humes H, Buffington D, MacKay S, et al. Replacement of renal function in uremic animals with a tissue-engineered kidney. Nature Biotech 17:451–455, 1999

[20] Humes H. Bioartificial kidney for full renal replacement therapy. Seminars in Nephrology 20:71–82, 2000

[21] Bone R C. Why sepsis trials fail. JAMA 276:565–566, 1996

[22] Bone R C. Toward a theory regarding the pathogenesis of the systemic inflammatory response syndrome: What we do and do not know about cytokine regulation. Critical Care Medicine 24:163–172, 1996

[23] Hack C E, Hart M, Strack van Schijndel R J, et al. Interleukin-8 in sepsis: Relation to shock and inflammatory mediators. Infection and Immunity 60:2835–2842, 1992

[24] Bone R C. Immunologic dissonance: A continuing evolution in our understanding of the systemic inflammatory response syndrome (SIRS) and the multiple organ dysfunction syndrome (MODS). Annals of Internal Medicine 125:680–687, 1996

[25] Bone R C, Grodzin C J, Balk R A. Sepsis: A new hypothesis for pathogenesis of the disease process. Chest 112:235–243, 1997

[26] Reeves J H, Butt W W, Shann F, et al. Continuous plasmafiltration in sepsis syndrome. Critical Care Medicine 27:2096–2104, 1999

[27] De Vriese A, Vanholder R, De Sutter J, et al. Continuous renal replacement therapies in sepsis: where are the data. Nephrology, Dialysis, Transplantation 13:13624, 1998

[28] Vincent J L, Spapen H, Bakker J, et al. Phase ii multicenter clinical study of the platelet-activating factor receptor antagonist bb-882 in the treatment of sepsis. Critical Care Medicine 28:638–642, 2000

[29] Quezado Z, Banks S, Natanson C. New strategies for combatting sepsis: the magic bullets missed the mark . . . but the search continues. Trends in Biotechnology 13:56–63, 1995

[30] Christman J W, Holden E P, Blackwell T S. Strategies for blocking the systemic effects of cytokines in the sepsis syndrome. Crit Care Med 23:955–963, 1995

[31] Kielar M, Jeyarajah D, Reed D, et al. The liver regulates renal ischemic injury: A possible role for renal il6 and hepatic il10? Abstract presented at poster session at American Society of Nephrology Annual Meeting, 2000

[32] Lally K, Cruz E, Xue H. The role of anti-tumor necrosis factor-alpha and interleukin-10 in protecting murine neonates from escherichia coli sepsis. Journal of Pediatric Surgery 35:852–854, 2000

[33] Walley K, Lukacs N, Standiford T, et al. Balance of inflammatory cytokines related to severity and mortality of murine sepsis. Infection & Immunity 64:4733–4738, 1996

[34] Matsumoto T, Tateda K, Miyazaki S, et al. Effect of interleukin-10 on gut-derived sepsis caused by pseudomonas aeruginosa in mice. Antimicrobial Agents & Chemotherapy 42:2853–2857, 1998

[35] Marchant A, Bruyns C, Vandenabeele P, et al. Interleukin-10 controls interferon-γ and tumor necrosis factor production during experimental endotoxemia. Eur J Immunol 24:1167–1171, 1994

[36] MacKay S, Funke A, Buffington, D, Humes, D. Tissue engineering of a Bioartificial renal tubule. ASAIO Journal 44:179–183, 1998

What is claimed is:

1. A method of treating a patient with SIRS syndrome, comprising:

contacting, outside of the kidney, at least a portion of the body fluid of the patient with renal tubule cells.

2. The method of claim 1, wherein the patient is septic.

3. The method of claim 1, wherein the body fluid is blood.

4. The method of claim 1, wherein the body fluid is plasma.

5. The method of claim 1, wherein the body fluid is ultrafiltrate of plasma.

6. The method of claim 1, wherein the body fluid is contacted in with the renal tubule cells ex vivo.

7. The method of claim 1, wherein the body fluid is contacted in with the renal tubule cells inside the body of the patient.

8. The method of claim 1, wherein the body fluid is contacted in with the renal tubule cells in a renal tubule assist device.

9. The method of claim 8, wherein the renal tubule assist device is ex vivo.

10. The method of claim 8, wherein the renal tubule assist device is implanted in the patient.

11. The method of claim 1, wherein the patient is also afflicted with renal disease.

12. The method of claim 11, wherein the patient is afflicted with end-stage renal disease.

13. The method of claim 11, wherein the patient is on hemo- or peritoneal dialysis.

14. The method of claim 1, wherein the patient is not afflicted with renal disease.

15. A method of treating a patient with SIRS, comprising:

removing a portion of body fluid from the patient, contacting the removed body fluid with renal tubule cells, and returning at least a portion of the body fluid which has been contacted with the renal tubule cells to the patient.

16. The method of claim 15, wherein the patient is septic.

17. The method of claim 15, wherein the body fluid is blood.

18. The method of claim 15, wherein the body fluid is ultrafiltrate of plasma.

19. The method of claim 15, wherein the body fluid is contacted in with the renal tubule cells in a renal tubule assist device.

20. The method of claim 15, wherein the patient is also afflicted with renal disease.

21. The method of claim 20, wherein the patient is afflicted with end-stage renal disease.

22. The method of claim 20, wherein the patient is on hemo- or peritoneal dialysis.

23. The method of claim 15, wherein the patient is not afflicted with renal disease.

* * * * *

UNITED STATES PATENT AND TRADEMARK OFFICE
CERTIFICATE OF CORRECTION

PATENT NO. : 6,653,131 B2
DATED : November 25, 2003
INVENTOR(S) : H. David Humes It is certified that error appears in the above-identified patent and that said Letters Patent is hereby corrected as shown below:

Column 1,
Line 13, "modem" should read -- modern --.

Column 2,
Line 1, "perfuision" should read -- perfusion --.

Column 3,
Line 51, "the 10 venous" should read -- the venous --;
Line 59, "extracapillary 15" should read -- extracapillary space --.

Column 5,
Line 59, "t-4" should read -- t = 4 --.

Column 12,
Line 36, "therefore A the" should read -- therefore the --.
Line 58, "474479" should read -- 474-479 --.

Column 14,
Line 6, "13:13624" should read -- 13: 1362-4 --.

Signed and Sealed this

Eleventh Day of May, 2004

JON W. DUDAS
*Acting Director of the United States Patent and Trademark Office*